(12) United States Patent
Zhao et al.

(10) Patent No.: US 11,907,624 B2
(45) Date of Patent: Feb. 20, 2024

(54) APPROACH FOR CHARACTERIZING PROPAGATION OF METALLIC SHORT CRACKS AND LONG CRACKS

(71) Applicant: TIANJIN UNIVERSITY, Tianjin (CN)

(72) Inventors: Lei Zhao, Tianjin (CN); Molin Su, Tianjin (CN); Yongdian Han, Tianjin (CN); Lianyong Xu, Tianjin (CN); Kangda Hao, Tianjin (CN)

(73) Assignee: TIANJIN UNIVERSITY, Tianjin (CN)

( * ) Notice: Subject to any disclaimer, the term of this patent is extended or adjusted under 35 U.S.C. 154(b) by 0 days.

(21) Appl. No.: 17/979,002

(22) Filed: Nov. 2, 2022

(65) Prior Publication Data
US 2024/0012958 A1 Jan. 11, 2024

(30) Foreign Application Priority Data
Jul. 11, 2022 (CN) .......................... 202210807104.8

(51) Int. Cl.
| | |
|---|---|
| *G06F 30/20* | (2020.01) |
| *G01N 33/20* | (2019.01) |
| *G01N 33/2045* | (2019.01) |
| *G06F 111/10* | (2020.01) |

(52) U.S. Cl.
CPC ......... *G06F 30/20* (2020.01); *G01N 33/2045* (2019.01); *G06F 2111/10* (2020.01)

(58) Field of Classification Search
CPC .. G06F 30/20; G06F 2111/10; G01N 33/2045
See application file for complete search history.

(56) References Cited

U.S. PATENT DOCUMENTS

| | | | | |
|---|---|---|---|---|
| 2016/0061699 | A1* | 3/2016 | Colladon | ............... G01N 3/068 356/402 |
| 2016/0299046 | A1* | 10/2016 | Xuan | ....................... G01N 3/08 |

FOREIGN PATENT DOCUMENTS

CN 109632489 * 4/2019

OTHER PUBLICATIONS

Wang et al, Influence of pores on crack initiation in monotonic tensile and cyclic loadings in lost foam casting A319 alloy by using 3D in-situ analysis. 2016.*

(Continued)

*Primary Examiner* — Mohamed Charioui
*Assistant Examiner* — Lynda Dinh

(57) ABSTRACT

A method for characterizing propagation of metallic short cracks and long cracks includes: acquiring crack tip opening displacement in a metallic notched sample under cyclic loading; acquiring crack tip opening displacement amount caused by a single monotonic tensile in the notched sample, and crack tip opening displacement caused by monotonic tensile in the notched sample under a maximum far-field stress; and based on an original Shyam model, constructing, according to the crack tip opening displacement amount and the crack tip opening displacement by obtaining yield strength of metals, a $T_m\varphi_c$ model for characterizing the propagation of short cracks and long cracks, where the $T_m\varphi_c$ model is used for representing the growth rate of short cracks and long cracks.

6 Claims, 2 Drawing Sheets

(56) References Cited

OTHER PUBLICATIONS

Nam et al, "Simulation of ductile fracture toughness test under monotonic and reverse cyclic loading" 2017.*

Zou Binlian, "Fatigue Crack Growth Rates in Friction Stir Welding Butt Joints and Computational Simulation based on AFGROW", Engineering Science, China Excellent Doctoral and Master's Thesis Full Text Database (Master), Part 1, pp. 18-21, Dec. 2011.

CNIPA, Notification of a First Office Action for CN202210807104.8, dated Aug. 17, 2022.

Tianjin University (Applicant), Reply to Notification of a First Office Action for CN202210807104.8, w/ (allowed) replacement claims, dated Aug. 23, 2022.

CNIPA, Notification to grant patent right for invention in CN202210807104.8, dated Aug. 29, 2022.

* cited by examiner

APPROACH FOR CHARACTERIZING PROPAGATION OF METALLIC SHORT CRACKS AND LONG CRACKS

CROSS-REFERENCE TO RELATED APPLICATION

This application claims priority to Chinese patent application No. 202210807104.8 filed on Jul. 11, 2022 and entitled "APPROACH FOR CHARACTERIZING PROPAGATION OF METALLIC SHORT CRACKS AND LONG CRACKS", the entire contents of which are incorporated herein by reference.

BACKGROUND OF THE INVENTION

1. Field of the Invention

The present invention relates to the technology field of calculation of fatigue crack growth rates, and in particular to an approach for characterizing propagation of metallic short cracks and long cracks.

2. Description of Related Art

With the increasing demand of high-end equipment in China, the incidence of fracture accidents increases. Fatigue is one of the main causes of structural fracture. Therefore, a stress intensity factor range, namely, a Paris law, is proposed to describe a crack growth rate. People attach great importance to the traditional Paris method, and apply to various materials. However, with further research, the limitations of this approach are revealed. For example, as a material system changes, a large number of metal fatigue crack propagation experiments are required to determine the fitting constants of C and m. In addition, the Paris law cannot describe the propagation of short cracks due to the crack closure effect and the existence of a plastic zone at crack tip, which leads to segmentation between a short crack propagation model and a macroscopic long crack propagation model, and the adoption of corresponding models to respectively obtain growth rates and life prediction of short cracks and long cracks. Therefore, there is a need to propose an approach for characterizing propagation of metallic short cracks and long cracks. Such approach is used in different materials, and is suitable for the propagation of short cracks and macroscopic long cracks, so as to simply and efficiently evaluate the fatigue performance of metal materials.

SUMMARY OF THE INVENTION

To solve the existing technical problems, the present invention aims to provide an approach for characterizing propagation of metallic short cracks and long cracks. Damage in the monotonic plastic zone in front of crack tip is calculated according to a crack tip blunting model, and then damage in the cyclic plastic zone ahead of crack tip is calculated according to a dislocation model, so as to determine a fatigue crack growth rate model, which provides important theoretical basis and industrial value for the calculation of the growth rates of short-long cracks of different metals, and is of great significance.

To achieve the above-mentioned technical objective, the present invention provides an approach for characterizing propagation of metallic short cracks and long cracks, including the following steps:

acquiring crack tip opening displacement in a metallic notched sample under cyclic loading;

acquiring crack tip opening displacement amount caused by a single monotonic tensile in the notched sample, and crack tip opening displacement caused by monotonic tensile in the notched sample under a maximum far-field stress;

based on an original Shyam model, constructing, according to the crack tip opening displacement amount and the crack tip opening displacement caused by monotonic tensile and by obtaining yield strength of the metals, a $T_{m\varphi c}$ model for characterizing the propagation of short cracks and long cracks, where the $T_{m\varphi c}$ model is used for representing the growth rate of short cracks and long cracks.

Preferably, the approach includes: in the process of acquiring crack tip opening displacement of a notched sample under cyclic loading, performing fatigue crack propagation experiment under different working conditions on notched samples of different metal materials; and acquiring the crack tip opening displacement according to a BCS continuous distributed model.

Preferably, in the process of acquiring the crack tip opening displacement, an expression of the crack tip opening displacement is:

$$\varphi_c = \frac{8\sigma_{ys}(1-v^2)a}{\pi E}\ln\left(\sec\left(\frac{(1-R)\pi\sigma_{max}}{4\sigma_{ys}}\right)\right)$$

where $\varphi_c$ represents the crack tip opening displacement under cyclic loading, R represents a stress ratio, V represents a Poisson's ratio, $\alpha$ represents a crack length, $\sigma_{ys}$ represents a material yield strength, $\sigma_{max}$ represents the maximum far-field stress, and E represents a Young's modulus.

Preferably, the approach includes: in the process of acquiring crack tip opening displacement amount, acquiring the crack tip opening displacement amount according to a Zheng-Hirt crack tip blunting model, where an expression of acquiring the crack tip opening displacement amount is:

$$da/dN = x = \frac{K_I^2}{\pi\sigma_{yy}^2}$$

in the expression, da/dN is a crack growth rate, $K_I$ is a stress intensity factor of I-shaped cracks, and $\sigma_{yy}$ represents an opening stress, which is equal to a material critical fracture stress.

Preferably, the approach includes: in the process of acquiring the crack tip opening displacement amount according to a Zheng-Hirt crack tip blunting model, considering a blunting crack tip as a micro-notch, and acquiring the material critical fracture stress according to a metallic notch cracking criterion, where an expression of the material critical fracture stress is:

$$K_t\sigma_{max} = \sqrt{E\sigma_f\varepsilon_f} = \sigma_{ff}$$

in the expression, $K_t$ is a theoretical stress concentration coefficient, $\sigma_f$ and $\varepsilon_f$ are respectively the true fracture stress and fracture ductility that are related to material section shrinkage, and $\sigma^{ff}$ represents the material critical fracture stress.

Preferably, the approach includes: in the process of acquiring crack tip opening displacement caused by monotonic tensile, acquiring the crack tip opening displacement caused by monotonic tensile based on a fracture mechanics theory and according to the material critical fracture stress and the crack tip opening displacement amount, where an expression of the crack tip opening displacement caused by monotonic tensile is:

$$\varphi_{mt} = \frac{K_{max}^2}{\pi E \sigma_f \varepsilon_f}$$

where $\varphi_{mt}$ represents the crack tip opening displacement caused by monotonic tensile, and $K_{max}$ represents the maximum far-field stress.

Preferably, the approach includes: after the process of acquiring the crack tip opening displacement caused by monotonic tensile, performing the following modification on the crack tip opening displacement caused by monotonic tensile based on influences of static toughness dissipation and strain energy releasing at crack tip on metallic fatigue damages:

$$T_m = \frac{\sigma_{ys}}{U_T}\varphi_{mt}$$

where $T_m$ is the crack tip opening displacement caused by monotonic tensile, which considers the static toughness dissipation and crack tip strain energy of metals, and $U_T$ is static toughness.

Preferably, the approach includes: in the process of constructing a $T_{m\varphi c}$ model for representing the propagation of short cracks and long cracks, based on the original Shyam model, constructing, according to the crack tip opening displacement amount and the modified crack tip opening displacement caused by monotonic tensile, the $T_{m\varphi c}$ model by acquiring the metallic yield strength.

Preferably, in the process of constructing the $T_{m\varphi c}$ model, an expression of the $T_{m\varphi c}$ model is:

$$da/dN = k(T_m \varphi_c)^{m2}$$

where k and $T_{m\varphi c}$ m2 represent fitting parameters.

Preferably, a characterization system for implementing the characterization approach, including:
a first data processing module, configured to acquire crack tip opening displacement in a metallic notched sample under cyclic loading;
a second data processing module, configured to acquire crack tip opening displacement amount caused by a single monotonic tensile in the notched sample, and crack tip opening displacement caused by monotonic tensile in the notched sample under a maximum far-field stress;
a growth rate characterization module, configured to: on the basis of an original Shyam model, construct, according to the crack tip opening displacement amount and the crack tip opening displacement caused by monotonic tensile and by obtaining yield strength of the metals, a $T_{m\varphi c}$ model for characterizing the propagation of short cracks and long cracks, where the $T_{m\varphi c}$ model is used for representing the growth rate of short cracks and long cracks.

The present invention discloses the following technical effects:

In the present invention, the crack tip opening displacements under monotonic tensile and cyclic loading are respectively calculated according to a crack tip blunting model and a dislocation theory, so as to uniformly describe the metallic growth rate of short cracks and long cracks. The whole testing process is of high precision and high efficiency, and has a wide application range, broad application prospects and economic benefits, which provides important theoretical basis and practice foundation for engineering material performance evaluation.

BRIEF DESCRIPTION OF THE DRAWINGS

To illustrate the technical solutions in embodiments of the present invention or in the prior art more clearly, the accompanying drawings that need to be used in the embodiments will be briefly introduced below. Obviously, the accompanying drawings in the following description are merely some embodiments of the present invention. For a person of ordinary skill in the art, other accompany drawings may be obtained from these accompany drawings without creative efforts.

DETAILED DESCRIPTION OF THE PREFERRED EMBODIMENTS

To make the objectives, technical solutions and advantages of the embodiments of the present application clearer, the technical solutions in the embodiments of the present application will be clearly and completely described below in conjunction with the accompanying drawings in the embodiments of the present application. Obviously, the described embodiments are only part of the embodiments of the present application, but not all embodiments. Components according to the embodiments of the present invention, which are generally described and shown in the accompanying drawings herein, may be arranged and designed in different configurations. Therefore, the following detailed descriptions of the embodiments of the present invention provided in the accompany drawings are not intended to limit the scope of the present application, but merely represent the selected embodiments of the present application. All the other embodiments obtained by a person skilled in the art without creative efforts based on the embodiments of this application shall fall within the protection scope of the present application.

Figure 1:
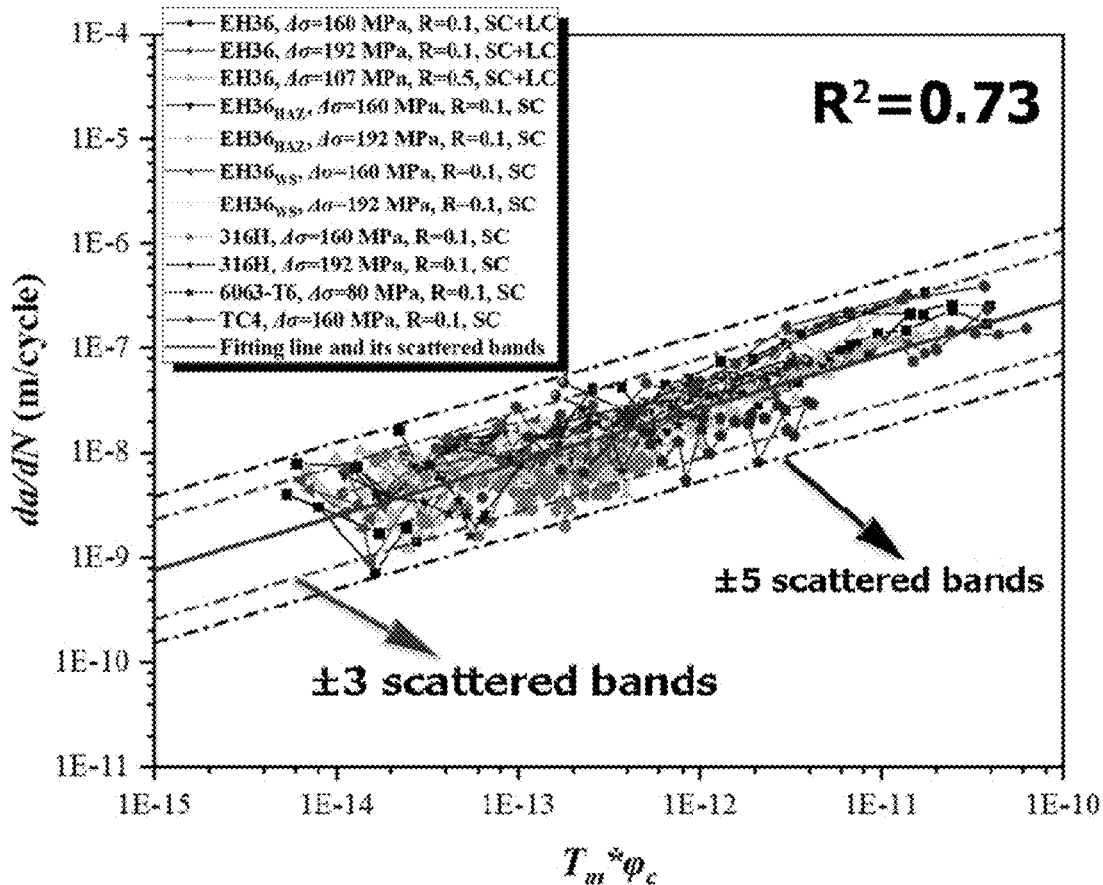
FIG. 1 is a diagram of crack growth rates of different materials described by the $T_{m\varphi c}$ model according to the embodiments of the present invention.
Figure 2:
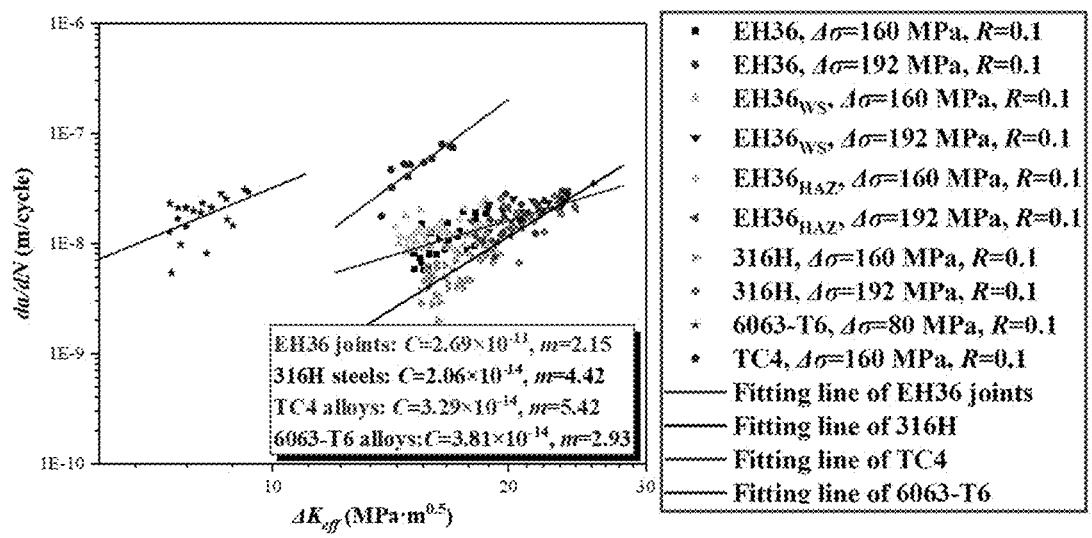
FIG. 2 is a diagram of crack growth rates of different materials described by the $\Delta K_{eff}$ model according to the embodiments of the present invention.
Figure 3:
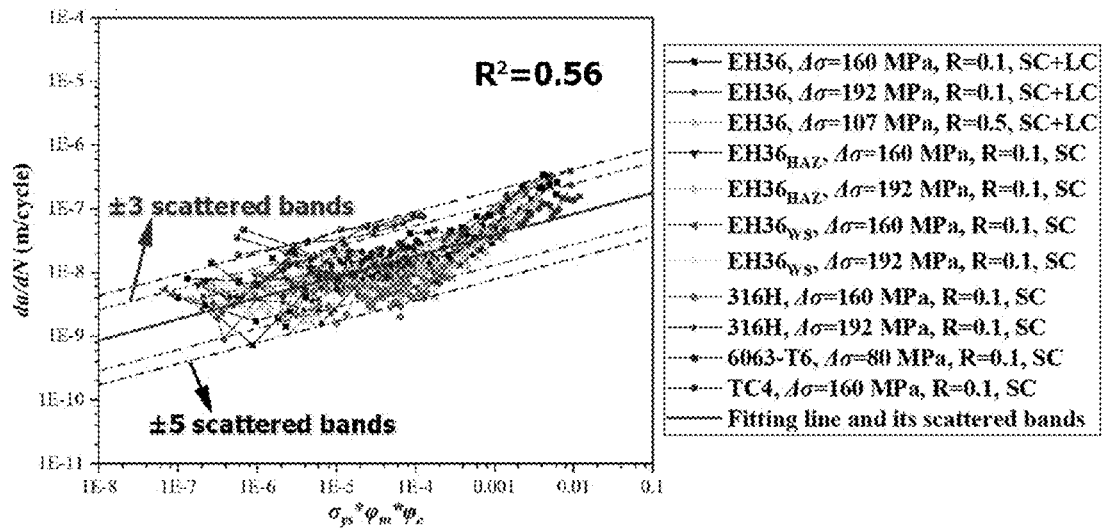
FIG. 3 is a diagram of crack growth rates of different materials described by the Shyam model according to the embodiments of the present invention.
Figure 4:
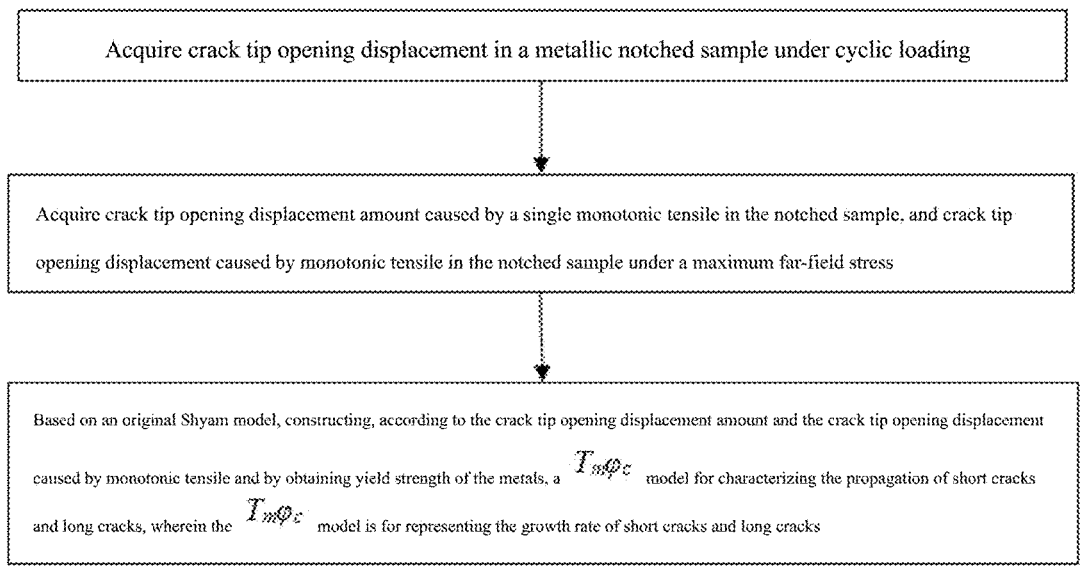
FIG. 4 is a schematic flowchart of the characterization approach according to the present invention.

As shown in FIG. 1 to FIG. 3, the present invention provides an approach for characterizing propagation of metallic short cracks and long cracks. The approach may include the following steps:

Step 1: Perform fatigue crack propagation experiment on a plurality of notched samples of a base metal, a heat-affected zone and a welded seam zone in EH36 joint, 316H austenitic stainless steel, 6063-T6 aluminum alloy, and TC4 titanium alloy, and calculate, by means of a BCS continuous distribution model, crack tip opening displacement $\varphi_c$ caused by cyclic loading:

$$\varphi_c = \frac{8\sigma_{ys}(1-v^2)a}{\pi E}\ln\left(\sec\left(\frac{(1-R)\pi\sigma_{max}}{4\sigma_{ys}}\right)\right) \quad (1)$$

where $\varphi_c$ is the crack tip opening displacement caused by cyclic loading, R is a stress ratio, v is a Poisson's ratio, α is a crack length, and $\sigma_{ys}$ is a material yield strength.

Step 2: Calculate, according to a Zheng-Hirt crack tip blunting model, crack tip opening displacement amount x caused by monotonic tensile per cycle:

$$da/dN = x = \frac{K_I^2}{\pi\sigma_{yy^2}} \quad (2)$$

where da/dN is the crack growth rate, $K_I$ is a stress intensity factor of I-shaped cracks, and $\sigma_{yy}$ represents opening stress, which is equal to a material critical fracture stress off.

If a blunting crack tip is considered as a micro-notch, formula (3) may be obtained according to a metallic notch cracking criterion:

$$K_t\sigma_{max} = \sqrt{E\sigma_f\varepsilon_f} = \sigma_{ff} \quad (3)$$

where $K_t$ is a theoretical stress concentration coefficient, E is a Young's modulus, $\sigma_f$ and $\varepsilon_f$ are respectively a true fracture stress and fracture ductility that are related to material section shrinkage, $\sigma_{ff}$ is the material critical fracture stress, and $\sigma_{max}$ is a maximum far-field stress.

Step 3: Crack tip opening displacement $\varphi_{mt}$ caused by monotonic tensile due to the maximum far-field stress may be obtained according to formulas (2) and (3) and a fracture mechanics theory:

$$\varphi_{mt} = \frac{K_{max}^2}{\pi E\sigma_f\varepsilon_f} \quad (4)$$

where $\varphi_{mt}$ is the crack tip opening displacement caused by monotonic tensile, and is mainly determined by the maximum far-field stress.

Step 4: Perform the following modification on $\varphi_{mt}$ by considering influences of static toughness dissipation and strain energy releasing at crack tip on fatigue damage of metals:

$$T_m = \frac{\sigma_{ys}}{U_T}\varphi_{mt} \quad (5)$$

where $T_m$ is the crack tip opening displacement caused by monotonic tensile, which considers the static toughness dissipation and crack tip strain energy of materials, and $U_T$ is static toughness.

Step 5: Calculate an expression of a short crack growth rate of the metals according to an original Shyam model and by using a product of the material yield strength and the crack tip opening displacements caused by monotonic loading and cyclic loading:

$$da/dN = u(\sigma_{ys}\varphi_m\varphi_c)^{m1} \quad (6)$$

where u and m1 are fitting parameters, and is the crack tip opening displacement that is caused by monotonic loading and calculated according to the BCS model.

$$\varphi_m = \frac{4\sigma_{ys}(1-v^2)a}{\pi E}\ln\left(\sec\left(\frac{(\pi\sigma_{max})}{2\sigma_{ys}}\right)\right) \quad (7)$$

Finally, modify $\sigma_{ys}\varphi_m$ in the Shyam original model to $T_m$, and obtain an expression uniformly describing the growth rates of short cracks and long cracks of metal materials:

$$da/dN = k(T_m\varphi_c)^{m2} \quad (8)$$

where k and m2 are fitting parameters.

It can be seen that the propagation behavior of short cracks and long cracks of different metal materials under different working conditions may be directly represented by a straight line by using $T_{m\varphi c}$, most of the data is within an error band 3, and short cracks SC and long cracks LC have a same slope, as shown in FIG. 1. The behavior of short cracks of a plurality of materials can only be described by using a conventional effective stress intensity factor $\Delta K_{eff}$ via a plurality of fitting lines, which is not universal for metal materials, as shown in FIG. 2. In FIG. 3, a Shyam model can only describe short cracks, and cannot uniformly describe the short cracks and long cracks, which has specific limitations, and is poor in both prediction accuracy and universality than $T_{m\varphi c}$.

According to the present invention, the crack tip opening displacements under monotonic tensile and cyclic loading are respectively calculated according to a crack tip blunting model and a dislocation theory, so as to uniformly describe the growth rates of short cracks and long cracks of metal materials. The whole testing process is of high precision and high efficiency, and has a wide application range, broad application prospects and economic benefits, which provides important theoretical basis and practice foundation for engineering material performance evaluation.

In the descriptions of the present specification, description of reference terms such as "one embodiment", "some embodiments", "examples", "specific examples", or "some examples" implies that specific characteristics, structures, materials or features described in conjunction with the embodiments or the examples are included in at least one embodiment or example of the present invention. In the present specification, the schematic expression of the above terms does not necessarily refer to the same embodiment or example. Moreover, the described specific characteristics, structures, materials or features can be combined in a suitable manner in any one or more embodiments or examples. In addition, a person skilled in the art may combine different embodiments or examples described in the present specification and features of different embodiments or examples without conflicting with each other.

In addition, terms such as "first" and "second" are used only for description, and cannot be understood as indicating or implying relative importance or implicitly indicating the number of indicated technical features. Therefore, the feature defining "first" and "second" may explicitly or implicitly include at least one feature. In the description of the present invention, "a plurality of" means at least two, for example, two, three, and the like, unless otherwise expressly and specifically limited.

The present invention is described with reference to flowcharts and/or block diagrams of methods, devices (systems), and computer program products according to the embodiments of the present invention. It should be understood that each flow and/or block in the flowcharts and/or block diagrams, and a combination of the flows and/or blocks in the flowcharts and/or block diagrams may be implemented by means of computer program instructions. These computer program instructions may be provided to processors of a general-purpose computer, a dedicated computer, an embedded processor, or other programmable data processing devices, so as to generate a machine, so that the instructions executed by the processors of the computer or other programmable data processing devices produce an apparatus for implementing functions specified in one or more flows in the flowcharts and/or one or more blocks in the block diagrams.

What is claimed is:

1. A method for characterizing propagation of metallic short cracks and long cracks, comprising the following steps:
   acquiring crack tip opening displacement in a metallic notched sample under cyclic loading, wherein the metallic notched sample comprises one of 316H austenitic stainless steel, 6063-T6 aluminum alloy and TC4 titanium alloy;
   acquiring crack tip opening displacement amount caused by a single monotonic tensile in the metallic notched sample, and crack tip opening displacement caused by monotonic tensile in the metallic notched sample under a maximum far-field stress;
   based on an original Shyam model, constructing, according to the crack tip opening displacement amount and the crack tip opening displacement caused by the monotonic tensile and by obtaining yield strength of the metallic notched sample, a $T_m \varphi_c$ model for characterizing the propagation of the metallic short cracks and long cracks, wherein the $T_m \varphi_c$ model is representing a growth rate of the metallic short cracks and long cracks;
   wherein an expression of the $T_m \varphi_c$ model is:

$$da/dN = k(T_m \varphi_c)^{m2}$$

wherein da/dN represents the growth rate of the metallic short cracks and long cracks, $\varphi_c$ represents the crack tip opening displacement under cyclic loading, $T_m$ is the crack tip opening displacement caused by the monotonic tensile under static toughness dissipation and crack tip strain energy of materials, and k and m2 represent fitting parameters; and
   wherein an expression of the crack tip opening displacement is:

$$\varphi_c = \frac{8\sigma_{ys}(1-v^2)a}{\pi E} \ln\left(\sec\left(\frac{(1-R)\pi\sigma_{max}}{4\sigma_{ys}}\right)\right)$$

wherein R represents a stress ratio, V represents a Poisson's ratio, α represents a crack length, $\sigma_{ys}$ represents a material yield strength, $\sigma_{max}$ represents the maximum far-field stress, and E represents a Young's modulus;
   wherein the method for characterizing the propagation of the metallic short cracks and long cracks further comprises: applying the $T_m \varphi_c$ model to characterize propagation behavior of metallic short cracks and long cracks of different metal materials to obtain growth rates and life prediction of the short cracks and long cracks on the different metal materials, thereby performing fatigue crack propagation experiment under different working conditions on notched samples of different metal materials as engineering material performance evaluation for equipment.

2. The method for characterizing the propagation of the metallic short cracks and long cracks according to claim 1, further comprising:
   acquiring the crack tip opening displacement according to a BCS continuous distribution model.

3. The method for characterizing the propagation of the metallic short cracks and long cracks according to claim 2, further comprising:
   in the process of acquiring crack tip opening displacement amount, acquiring the crack tip opening displacement amount according to a Zheng-Hirt crack tip blunting model, wherein an expression of acquiring the crack tip opening displacement amount is:

$$da/dN = x = \frac{K_I^2}{\pi \sigma_{yy}^2}$$

in the expression, is a stress intensity factor of I-shaped cracks, and $\sigma_{yy}$ represents an opening stress, which is equal to a material critical fracture stress, and x represents the crack tip opening displacement amount.

4. The method for characterizing the propagation of the metallic short cracks and long cracks according to claim 3, further comprising:
   in the process of acquiring the crack tip opening displacement amount according to a Zheng-Hirt crack tip blunting model, taking a blunting crack tip as a micro-notch, and acquiring the material critical fracture stress according to a metallic notch cracking criterion, wherein an expression of the material critical fracture stress is:

$$K_t \sigma_{max} = \sqrt{E\sigma_f \varepsilon_f} = \sigma_{ff}$$

in the expression, $K_t$ is a theoretical stress concentration coefficient, $\sigma_f$ and $\varepsilon_f$ are respectively a true fracture stress and fracture ductility that are related to material section shrinkage, and $\sigma_{ff}$ represents the material critical fracture stress.

5. The method for characterizing the propagation of the metallic short cracks and long cracks according to claim 4, further comprising:
   in the process of acquiring crack tip opening displacement caused by monotonic tensile, acquiring the crack tip opening displacement caused by the monotonic tensile based on a fracture mechanics theory and according to the material critical fracture stress and the crack tip opening displacement amount, wherein an expression of the crack tip opening displacement caused by monotonic tensile is:

$$\varphi_{mt} = \frac{K_{max}^2}{\pi E \sigma_f \varepsilon_f}$$

wherein $\sigma_{mt}$ represents the crack tip opening displacement caused by the monotonic tensile, and $K_{max}$ represents the maximum far-field stress.

6. The method for characterizing the propagation of the metallic short cracks and long cracks according to claim 5, further comprising:
   after the process of acquiring the crack tip opening displacement caused by monotonic tensile, performing a modification on the crack tip opening displacement caused by monotonic tensile based on influences of static toughness dissipation and strain energy releasing at crack tip on fatigue damage of metal materials, wherein an expression of the modification is:

$$T_m = \frac{\sigma_{ys}}{U_T}\varphi_{mt}$$

wherein $U_T$ is static toughness.

* * * * *